(12) United States Patent
Sillitoe et al.

(10) Patent No.: US 11,644,138 B2
(45) Date of Patent: May 9, 2023

(54) CLAMP

(71) Applicant: Bio Pure Technology Limited, Waterlooville (GB)

(72) Inventors: Chris Sillitoe, Cardiff (GB); Nick White, Falmouth Cornwall (GB)

(73) Assignee: Bio Pure Technology Limited, Waterlooville (GB)

( * ) Notice: Subject to any disclaimer, the term of this patent is extended or adjusted under 35 U.S.C. 154(b) by 384 days.

(21) Appl. No.: 17/049,767

(22) PCT Filed: Apr. 3, 2019

(86) PCT No.: PCT/EP2019/058440
§ 371 (c)(1),
(2) Date: Oct. 22, 2020

(87) PCT Pub. No.: WO2019/206590
PCT Pub. Date: Oct. 31, 2019

(65) Prior Publication Data
US 2021/0247008 A1 Aug. 12, 2021

(30) Foreign Application Priority Data
Apr. 27, 2018 (GB) ...................................... 1806906

(51) Int. Cl.
*F16L 23/04* (2006.01)
*F16L 37/088* (2006.01)

(52) U.S. Cl.
CPC ......... *F16L 37/088* (2013.01); *F16L 2201/10* (2013.01); *F16L 2201/44* (2013.01)

(58) Field of Classification Search
CPC . F16L 21/06; F16L 23/04; F16L 23/12; F16L 23/08; F16L 23/10; F16L 33/03;
(Continued)

(56) References Cited

U.S. PATENT DOCUMENTS

| 2008/0093844 A1* | 4/2008 | Casey | F16L 23/22 |
| | | | 285/135.2 |
| 2009/0119886 A1* | 5/2009 | Werth | F16L 23/04 |
| | | | 24/193 |

(Continued)

FOREIGN PATENT DOCUMENTS

| EP | 926414 A2 | 6/1999 |
| EP | 2065628 A2 | 6/2009 |

(Continued)

OTHER PUBLICATIONS

International Search Report and Written Opinion for Application PCT/EP2019/058440 dated Jul. 10, 2019.
(Continued)

*Primary Examiner* — Aaron M Dunwoody
(74) *Attorney, Agent, or Firm* — Honigman LLP

(57) ABSTRACT

A clamp comprises a first arcuate portion, a second arcuate portion connected to the first arcuate portion via a hinge, and a ratchet mechanism for locking the first and second arcuate portions in a closed position. The first and second arcuate portions each comprise a circumferential groove which tapers in a radial direction from an opening of the groove to a base of the groove. The groove of one of the first and second arcuate portions has an angular extent which exceeds 180 degrees and has an opening with a width which is narrower at opposing ends of the groove than at a position partway between the ends.

4 Claims, 4 Drawing Sheets

(58) Field of Classification Search
CPC ....... F16L 33/035; F16L 33/22; F16L 37/088; F16L 47/14; Y10T 24/1406; Y10T 24/14
See application file for complete search history.

(56) References Cited

U.S. PATENT DOCUMENTS

| | | | | |
|---|---|---|---|---|
| 2009/0208277 A1* | 8/2009 | Werth | ................. | A61M 39/1011 403/312 |
| 2010/0132165 A1* | 6/2010 | Shor | ................... | F16L 37/1225 24/19 |
| 2011/0163533 A1* | 7/2011 | Snyder | ................. | F16L 33/035 285/88 |
| 2012/0227221 A1* | 9/2012 | Whitaker | ........... | A61M 39/1011 29/525.08 |
| 2013/0249212 A1* | 9/2013 | McKiernan | ............. | F16L 23/10 285/407 |
| 2016/0053926 A1* | 2/2016 | Whitaker | ................ | F16L 37/12 285/34 |
| 2017/0248258 A1* | 8/2017 | Kuo | .......................... | F16B 2/10 |
| 2018/0156362 A1* | 6/2018 | Takeda | ................... | F16L 43/02 |

FOREIGN PATENT DOCUMENTS

| | | |
|---|---|---|
| GB | 2549519 A | 10/2017 |
| GB | 2549564 A | 10/2017 |

OTHER PUBLICATIONS

United Kingdom Search Report for Application GB1806906.2 dated Oct. 25, 2018.
Korean Office Action, Application No. 10-2020-7033504, dated Aug. 30, 2022.
Canadian Intellectual Property Office First Examination Report, Application No. 3097799, dated Jan. 24, 2022.
Brazil Examination Report, Application No. BR112020020581-8 dated Jan. 5, 2023.

* cited by examiner

CLAMP

CROSS REFERENCE TO RELATED APPLICATIONS

This U.S. patent application claims priority under 35 U.S.C. § 371 to Patent Cooperation Treaty Application No. PCT/EP2019/058440, filed on Apr. 3, 2019, which claims the benefit of earlier-filed Great Britain Application No. GB1806906.2, filed on Apr. 27, 2018. The disclosures of these prior applications are considered part of the disclosure of this application and are hereby incorporated by reference in their entireties.

TECHNICAL FIELD

The invention relates to a clamp, particularly but not exclusively for connecting flanged tubes or connectors for use in the bio-technology, pharmaceutical and food industries.

BACKGROUND

The ability to quickly and effectively make fluid-tight connections between sanitary fittings is particularly important in the bio-technology, pharmaceutical and food industries where the fluid being conveyed must be isolated from the external environment in order to retain the sterile conditions.

For example, a tri-clamp fitting may be employed to connect a pair of hose tail fittings which are each inserted in a hose. A tri-clamp fitting generally comprises two semi-circular portions which are hingedly connected to one another. The free end of one of the semi-circular portions comprises a wingnut located on a bolt which can pivot relative to the semi-circular portion. The other semi-circular portion comprises a bifurcated portion which defines a slot that receives the bolt. The wingnut can be drawn into engagement with the bifurcated portion so as to lock the clamp in a closed position. The semi-circular portions comprise an inwardly facing tapered groove for drawing flanges of the hose tail fittings into sealing engagement, typically with a gasket therebetween.

SUMMARY

In accordance with an aspect of the invention there is provided a clamp comprising: a first arcuate portion; a second arcuate portion connected to the first arcuate portion via a hinge; and a ratchet mechanism for locking the first and second arcuate portions in a closed position; wherein the first and second arcuate portions each comprise a circumferential groove which tapers in a radial direction from an opening of the groove to a base of the groove; wherein the groove of one of the first and second arcuate portions has an angular extent which exceeds 180 degrees and has an opening with a width which is narrower at opposing ends of the groove than at a position partway between the ends.

The base of the groove may have a constant width between the opposing ends.

The opening of the groove may be widest midway between the opposing ends.

The ratchet mechanism may comprise a linear rack provided with the second arcuate portion and a pawl provided with the first arcuate portion for receiving the linear rack. The linear rack may comprise one or more asymmetrical teeth and the pawl may comprise a finger which is configured to engage with the teeth of the linear rack.

The clamp may be formed from a reinforced polymeric materials.

BRIEF DESCRIPTION OF THE DRAWINGS

For a better understanding of the invention, and to show more clearly how it may be carried into effect, reference will now be made, by way of example, to the accompanying drawings, in which:—

DETAILED DESCRIPTION

Figure 1:
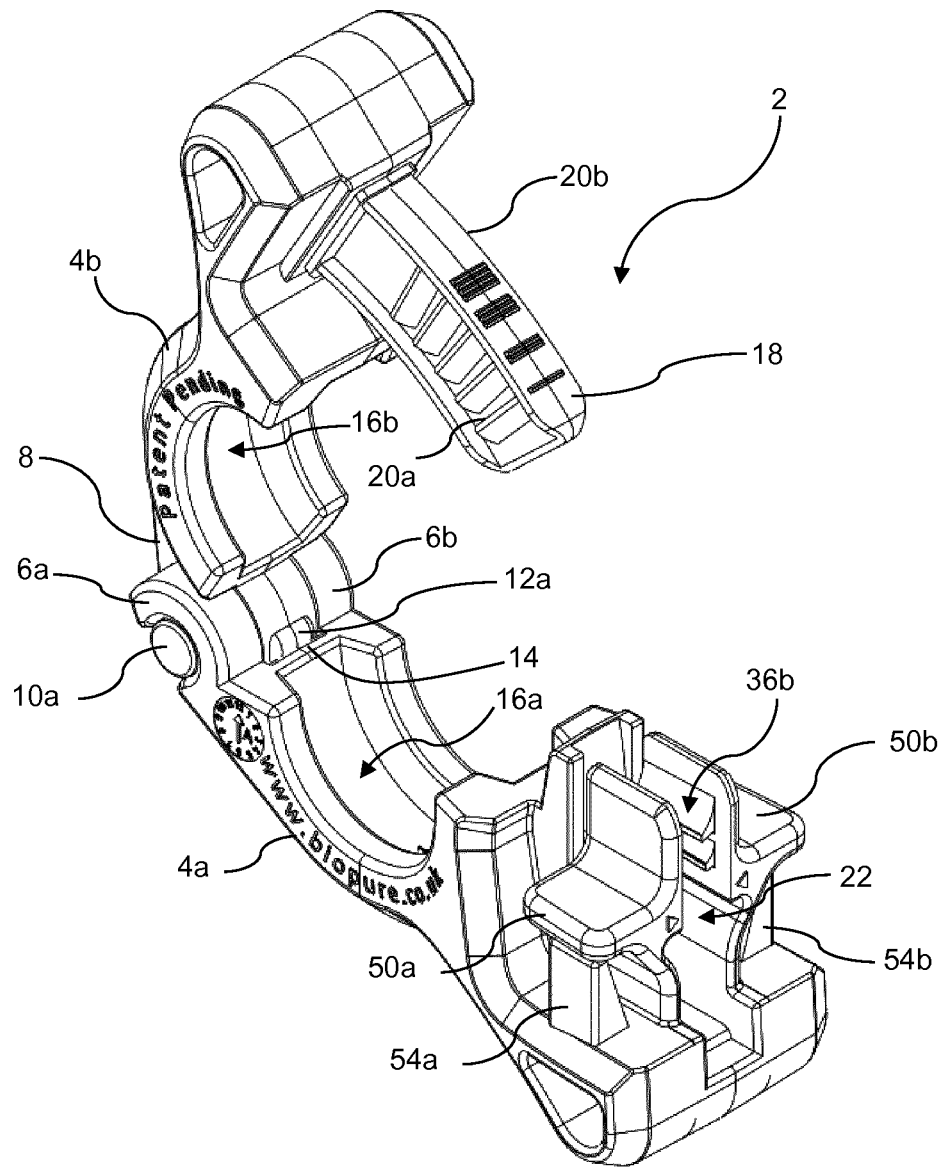
FIG. 1 is a perspective view of a clamp according to an embodiment of the invention in an open position.
Figure 2:
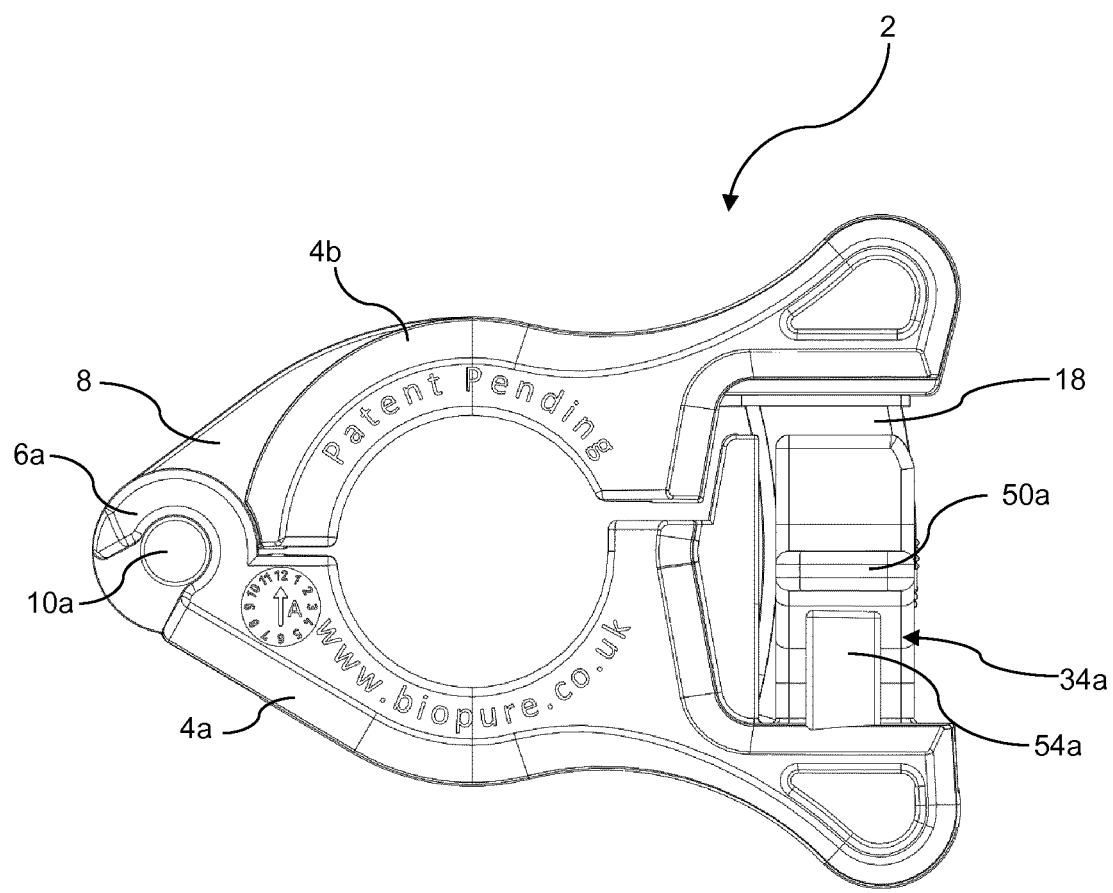
FIG. 2 is a side view of the clamp of FIG. 1 in a closed position.

FIGS. 1 and 2 show a clamp 2 according to an embodiment of the invention. The clamp 2 comprises a first, lower arcuate portion 4a and a second, upper arcuate portion 4b.

The first and second arcuate portions 4a, 4b are hingedly connected to one another. Specifically, the first arcuate portion 4a comprises a pair of hinge arms 6a, 6b which are spaced laterally from one another. The hinge arms 6a, 6b are arcuate and have extent which is slightly greater than 180°. The hinge arms 6a, 6b thus define a recess.

The second arcuate portion 4b is provided with a hinge lobe 8. A cylindrical stub shaft 10a, 10b projects from each lateral side of the hinge lobe 8. The stub shafts 10a, 10b are sized to be received within the recess defined by the hinge arms 6a, 6b to form a snap-fit connection. The first and second arcuate portions 4a, 4b are thus able to rotate between a closed position, as shown in FIG. 1, and an open position, as shown in FIG. 2.

Figure 3:
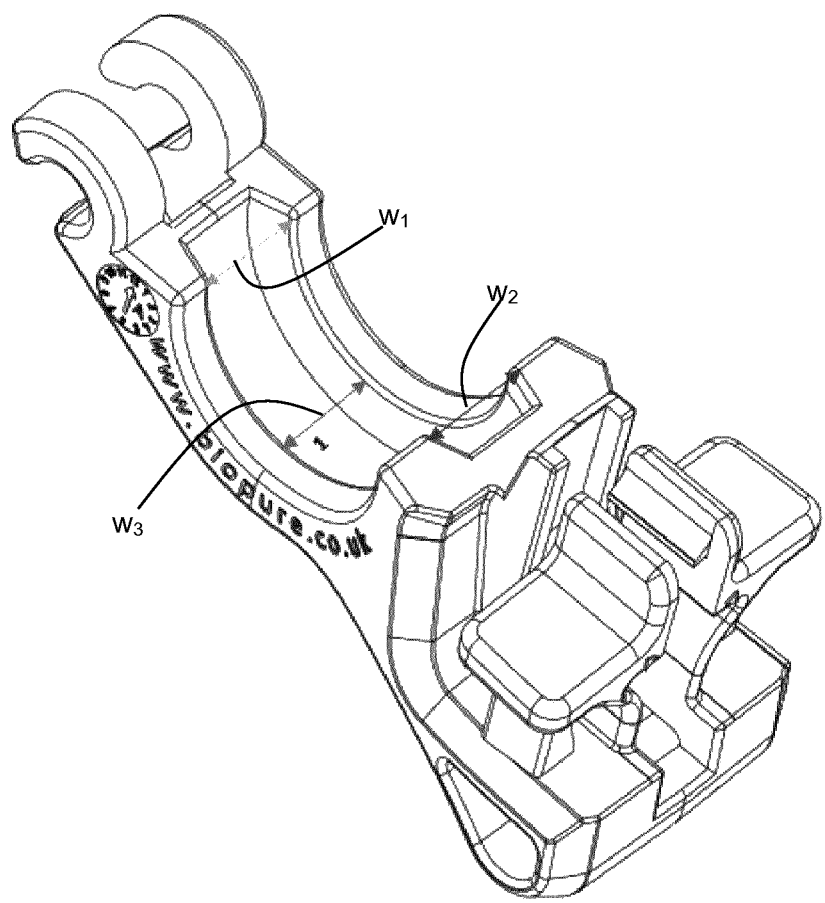
FIG. 3 is a perspective view of a lower portion of the clamp.

A radial, end surface of the hinge lobe 8 is provided with a pair of detent protrusions 12a, 12b which are angularly spaced from one another about the hinge lobe 8. The detent protrusions 12a, 12b (only one protrusion, protrusion 12a, is visible in FIG. 1 with the other being obscured behind the first arcuate portion 4a) interface with an edge 14 of the first arcuate portion 4a. Specifically, when opening the clamp 2, the detent protrusion 12a must be forced over the edge 14, such that the detent protrusions 12a, 12b straddle the edge 14, as is best shown in FIG. 3. In this position, the detent protrusion 12a prevents the clamp 2 from closing and the detent protrusion 12b prevents the clamp 2 from opening further. Thus, the detent protrusions 12a, 12b retain the clamp in the open position to improve ease of use. The clamp 2 may, however, be opened further in order to release the stub shafts 10a, 10b from the hinge arms 6a, 6b in order to detach the second arcuate portion 4b from the first arcuate portion 4a by applying sufficient force to force the detent protrusion 12b over the edge 14. Similarly, the clamp can be closed by applying sufficient force to force the detent protrusion 12a over the edge 14. The detent protrusions 12a, 12b may be allowed to pass over the edge 14 through deformation of the clamp 2. For example, deformation may occur in one or more of: the detent protrusions 12a, 12b, edge 14, the stub shafts 10a, 10b and the hinge arms 6a, 6b. The detent protrusions 12a, 12b may be movable and biased outwardly by a biasing mechanism, such as a spring or the like, such that deformation of the detent protrusions 12a, 12b is permitted by deformation of the biasing mechanism.

The distal, free ends of the first and second arcuate portions 4a, 4b are provided with a ratchet mechanism for locking the clamp 2 in the closed position. Specifically, the second arcuate portion 4b is provided with a tongue 18 (rack) which projects from the second arcuate portion 4b in a substantially circumferential direction. The tongue 18 comprises opposing lateral surfaces 20a, 20b which are each provided with one or more teeth.

The first arcuate portion 4a is provided with a receiving portion 22 which receives the tongue 18. The receiving portion 22 is defined by pawl portions 34a, 34b at either lateral side of the clamp 2. The pawl portions 34a, 34b are connected only at their lower ends. The pawl portions 34a, 34b are therefore cantilevered and are allowed to pivot about their lower ends. A release tab 50a, 50b protrudes perpendicularly from each pawl portion 34a, 34b.

Each of the pawl portions 34a, 34b is provided with a pair of fingers 36a, 36b (only the pair of fingers 36b is visible in FIG. 1; only one finger may be used in other embodiments) which are spaced from the hinged ends of the pawl portion 34a, 34b. The fingers 36a, 36b are configured to engage with the teeth of the opposing lateral surfaces 20a, 20b of the tongue 18 respectively.

The tongue 18 is curved along its length so that the teeth are kept parallel to the fingers 36a, 36b during rotation of the second arcuate portion 4b about the hinge.

Each pair of fingers 36a, 36b forms a primary, upper finger and a secondary, lower finger. The primary finger may be larger than the secondary finger. The primary finger may be used predominantly when the clamp is closed. The secondary finger engages with the tongue 18 and is used to increase the contact area when the clamp is under pressure. This effectively spreads the load between the two fingers, and acts as a backup in the unlikely event that the primary finger slips. A rib may be provided between the fingers at the innermost edge so as to join the fingers together. This rib reinforces both fingers and prevents deformation during pressurization following an autoclaving procedure. A corresponding slot may be provided in the tongue 18 to receive the rib between the fingers 36a, 36b.

The pawl portions 34a, 34b are cranked so that when vertical force is applied to the release tabs 50a, 50b, the pawl portions 34a, 34b move away from the tongue 18. This reduces the forces required to open the clamp.

A pair of tab stops 54a, 54b are provided to limit movement of the pawl portions 34a, 34b. The tab stops 54a, 54b are disposed beneath the release tabs 50a, 50b respectively and contact the release tabs 50a, 50b when they are pulled down to open the clamp 2. The tab stops 54a, 54b therefore prevent the pawl portions 34a, 34b from being opened excessively which could otherwise cause them to be permanently deformed. The tab stops 54a, 54b also serve a secondary purpose in that they prevent the user from placing their fingers under the release tabs 50a, 50b and thus convey to the user the correct way of opening the clamp.

As shown in FIG. 1, the radial, end surface of the tongue 18 may comprise a graduated scale or other indicia along its length which is visible between the pawl portions 34a, 34b and thus provides an indication of the position of the tongue 18 within the receiving portion 22 and thus the relative positions of the arcuate portions 4a, 4b. The scale can therefore be used to ensure that the clamp 2 has been closed sufficiently. The pawl portions 34a, 34b may be provided with reference indicia such as arrows which are used to define the relative position of the scale on the tongue 18.

The first and second arcuate portions 4a, 4b each comprise a substantially semi-circular (circumferential) groove 16a, 16b. Side walls of the grooves 16a, 16b are angled with respect to one another such that the width of the groove tapers in a radial direction (i.e. the groove is narrower at a larger radius than at a smaller radius) from its opening to its base. In the closed position shown in FIG. 2, the semi-circular grooves 16a, 16b of the first and second arcuate portions 4a, 4b meet to form a substantially continuous circular channel.

FIG. 3 shows the lower arcuate portion 4a in isolation. Although the base of the groove 16a (i.e. at the radially outer extent of the groove 16a) may have a consistent width along the length of the groove, the width of the opening to the groove (at its radially inner extent i.e. the widest part of the groove 16a) may vary along its length. Specifically, as shown in FIG. 3, the opening of the groove 16a may have a first width $w_1$ at a first end of the groove 16a adjacent the hinge end (i.e. near the hinge arms 6a, 6b), a second width $w_2$ at a second end of the groove 16a adjacent the ratchet end (i.e. near the receiving portion 22) and opposite to the first end, and a third width $w_3$ at the middle of the groove midway between the first and second ends of the groove 16a. The third width $w_3$ is greater than the first and second widths $w_1$, $w_2$. The first and second widths $w_1$, $w_2$ may be the same. The width of the opening to the groove thus increases from the first end adjacent the hinge to the midpoint of the groove 16a and then reduces in width towards the second end adjacent the ratchet mechanism.

Figure 4:
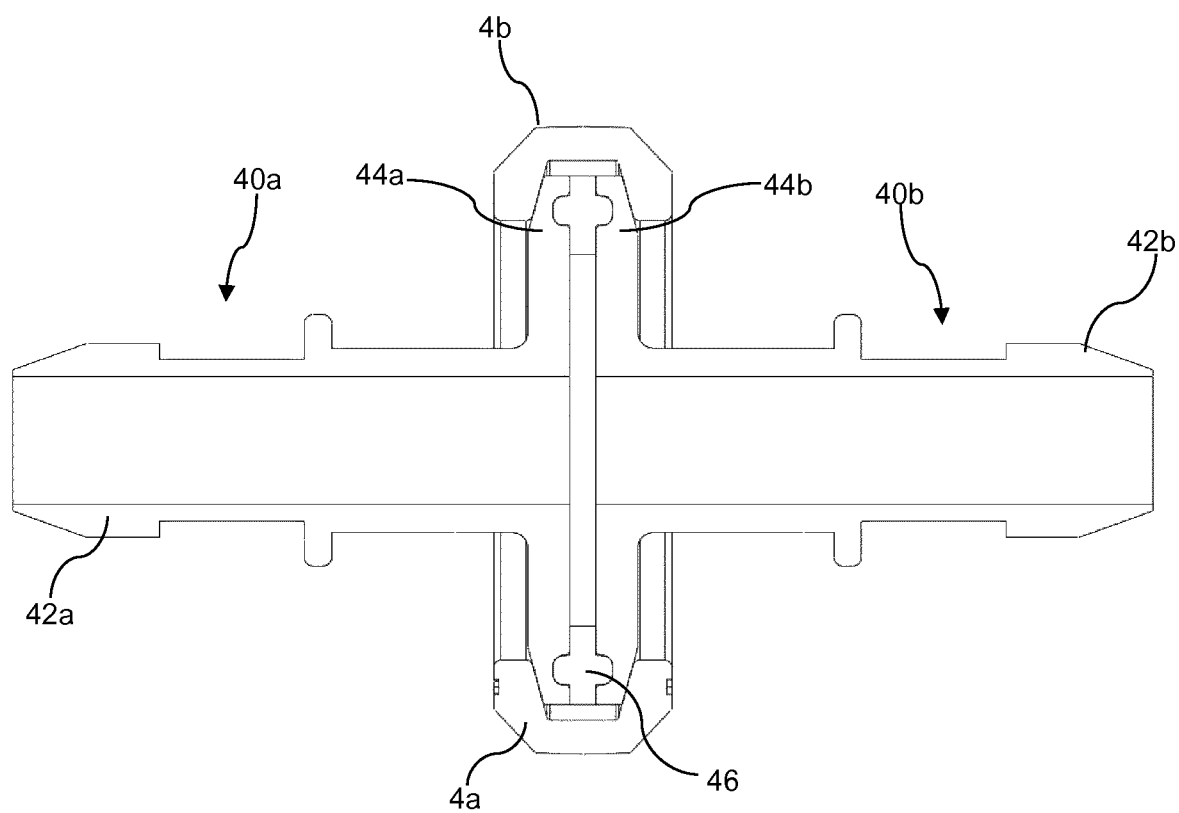
FIG. 4 is a cross-sectional view of the clamp in use.

As shown in FIG. 4, the clamp 2 may be employed to connect a pair of hose tail fittings 40a, 40b used to join two sections of hose together. The tail fittings 40a, 40b comprise a barb 42a, 42b which is inserted into the hose and a flange 44a, 44b.

In use, with the clamp 2 in the open position shown in FIG. 2, the flanges 44a, 44b are received in the semi-circular groove 16a of the first arcuate portion 4a with a gasket seal 46 disposed therebetween. As shown, the opposing surfaces of the flanges 44a, 44b may be provided with circular grooves for receiving the gasket seal 46. The clamp 2 is then closed such that the second arcuate portion 4b is received over the flanges 44a, 44b. In this closed position, the tongue 18 is received in the receiving portion 22 and the teeth of the tongue 18 engage with the fingers 36a, 36b of the pawl element 28.

The teeth of the tongue 18 are asymmetrical such that the fingers 36a, 36b ride over the teeth as the tongue 18 is inserted into the receiving portion 22, but engage with the teeth if the tongue 18 is retracted from the receiving portion 22. The first and second arcuate portions 4a, 4b can therefore be squeezed together such that the teeth progressively pass the fingers 36a, 36b. Owing to the tapered geometry of the grooves 16a, 16b, this action causes the flanges 44a, 44b to be forced toward one another, compressing the gasket seal 46 disposed therebetween. The clamp 2 is therefore able to provide a fluid-tight seal between the tail fittings 40a, 40b and the ratchet mechanism ensures that the first and second arcuate members 4a, 4b are retained in the closed position at the desired level of compression.

As shown in FIG. 2, the lower arcuate portion 4a does in fact have an angular extent which exceeds 180 degrees. In other words, the first and second arcuate portions 4a, 4b are not equal halves, with the first arcuate portion 4a extending over 192 degrees. This helps retain the components prior to clamping.

As described previously, the opening to the groove 16a is wider at the center than at the ends. The opposing ends of the groove 16a are typically the area of first contact with the flanges 44a, 44b of the fittings 40a, 40b when they are assembled in the clamp 2. Conversely they are last area of contact when the flanges 44a, 44b are removed (or escape) from the clamp 2. Employing a groove 16a with a narrower width opening at either end (in combination with an angular extent which exceeds 180 degrees) provides better retention of the fittings 40a, 40b. This means that the lower arcuate portion 4a by itself is able to hold two fittings and a compressed gasket seal in its groove without coming apart. This feature is very useful to assembly operators as it allows them to free a hand to perform another task e.g. close the clamp.

It will be appreciated that the profile of the groove 16a described above may also be used on groove 16b of the upper arcuate portion 4b. The groove is narrowed at its ends, but it is not necessary that the widest point of the groove lies midway between the two ends. The width of the opening of the groove may reduce smoothly from the center towards the ends or the groove may instead include a central section with a constant width and two sections either side of the central section which have a smaller width with a transition therebetween.

The geometry of the groove 16a described above may be used with clamps having different ratchet mechanisms and hinge structures to those described above.

To avoid unnecessary duplication of effort and repetition of text in the specification, certain features are described in relation to only one or several aspects or embodiments of the invention. However, it is to be understood that, where it is technically possible, features described in relation to any aspect or embodiment of the invention may also be used with any other aspect or embodiment of the invention.

It will be appreciated that the first and second arcuate portions need not be semi-circular and that additional (arcuate or non-arcuate) portions may be disposed between the first and second arcuate portions. The second arcuate portion may therefore be hingedly connected to the first arcuate portion via one or more additional portions.

The invention is not limited to the embodiments described herein, and may be modified or adapted without departing from the scope of the present invention.

The invention claimed is:

1. A clamp comprising:
   a first arcuate portion;
   a second arcuate portion connected to the first arcuate portion via a hinge; and
   a ratchet mechanism for locking the first and second arcuate portions in a closed position;
   wherein the first and second arcuate portions each comprise a circumferential groove which tapers in a radial direction from an opening of the groove to a base of the groove;
   wherein the groove of one of the first and second arcuate portions has an angular extent which exceeds 180 degrees and has an opening with a width which is narrower at opposing ends of the groove than at a position partway between the ends.

2. A clamp as claimed in claim 1, wherein the base of the groove has a constant width between the opposing ends.

3. A clamp as claimed in claim 1, wherein the opening of the groove is widest midway between the opposing ends.

4. A clamp as claimed in claim 1, wherein the ratchet mechanism comprises a linear rack provided with the second arcuate portion and a pawl provided with the first arcuate portion for receiving the linear rack;
   wherein the linear rack comprises one or more asymmetrical teeth and the pawl comprises a finger which is configured to engage with the teeth of the linear rack.

* * * * *